United States Patent [19]
Alvarez et al.

[11] Patent Number: 5,649,540
[45] Date of Patent: Jul. 22, 1997

[54] TONGUE POSITIONING DEVICE FOR MEDICAL PROCEDURES

[75] Inventors: Ramiro M. Alvarez, Fremont; Lawrence J. Barcelo, Salinas; Faustino Bernadett, Rolling Hills; Susan J. Lea, Berkeley, all of Calif.

[73] Assignee: Snorex, Inc., Reno, Nev.

[21] Appl. No.: 223,198

[22] Filed: Apr. 5, 1994

Related U.S. Application Data

[63] Continuation-in-part of Ser. No. 180,262, Jan. 12, 1994, abandoned.

[51] Int. Cl.$^6$ .................................................. A61F 5/56
[52] U.S. Cl. ............................................. 128/848; 128/860
[58] Field of Search ...................... 128/848, 857, 128/858, 859, 860, 861, 862, 200.26

[56] References Cited

U.S. PATENT DOCUMENTS

| | | | |
|---|---|---|---|
| 746,869 | 12/1903 | Moulton | 128/848 |
| 1,635,272 | 7/1927 | Härtl | 128/848 |
| 4,169,473 | 10/1979 | Samelson | 128/136 |
| 4,304,227 | 12/1981 | Samelson | 128/136 |
| 4,425,911 | 1/1984 | Luomanen et al. | 128/862 |
| 4,495,945 | 1/1985 | Liegner | 128/862 |
| 4,593,686 | 6/1986 | Lloyd et al. | 128/136 |
| 4,676,240 | 6/1987 | Gardy | 128/207 |
| 4,997,182 | 3/1991 | Kussick | 128/861 |
| 5,117,816 | 6/1992 | Shapiro et al. | 128/848 |
| 5,154,184 | 10/1992 | Alvarez | 128/848 |
| 5,316,020 | 5/1994 | Truffer | 128/848 |

OTHER PUBLICATIONS

Lowe, Dental Appliances for the Treatment of Snoring and Obstructive Sleep Apnea, Principle and Practices of Sleep Medicine, 2nd Ed. pp. 722–735, 1993.

*Primary Examiner*—Jessica J. Harrison
*Assistant Examiner*—Michael O'Neill

[57] ABSTRACT

A tongue positioning apparatus comprising a shield attached to a tongue receptacle for moving the user's tongue forward to provide access to the user's oropharynx during a medical procedure and a tube configured to receive an elongated device secured to the receptacle. The invention also comprises a method of performing a medical procedure including placing the tongue positioning apparatus on a patient's tongue, introducing a device through the tube and performing a medical procedure. Preferably, the procedure may comprise administering a gaseous anesthetic, intubating the patient or performing an endoscopic operation.

11 Claims, 9 Drawing Sheets

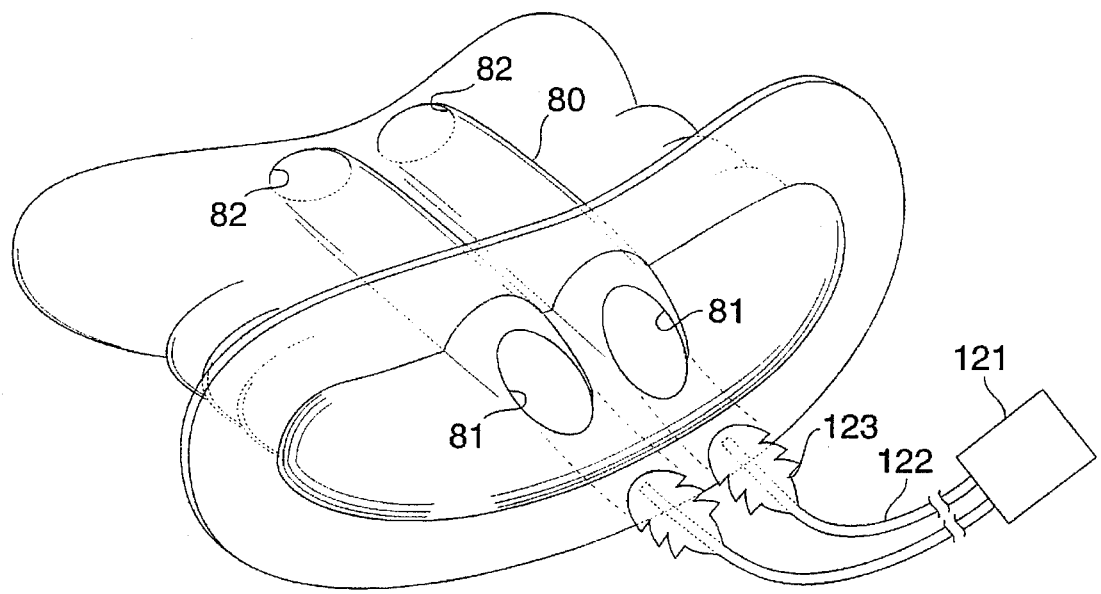
FIG. 12B
FIG. 13
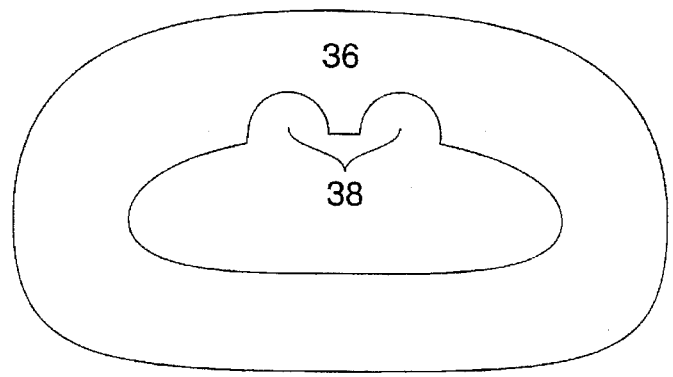
FIG. 14A
FIG. 14B

TONGUE POSITIONING DEVICE FOR MEDICAL PROCEDURES

CROSS-REFERENCE TO RELATED APPLICATIONS

This application is a continuation-in-part of application Ser. No. 08/180,262, filed Jan. 12, 1994, now abandoned, and entitled Adjustable Anti-Snoring Device.

FIELD OF THE INVENTION

This invention relates generally to apparatus for positioning a patient's tongue as an adjunct to various medical procedures. More particularly, it concerns improvements in tongue-position control and breathing enhancements for anesthesia, post-anesthesia, conscious sedation, oral surgery, and endoscopic procedures.

Background of the Invention

Breathing is fundamental to maintaining human life. Some of our most fundamental reflexes involve breathing and maintaining a patent airway. Anything that interferes with breathing may constitute a life-threatening situation. For example, an unconscious or semi-conscious person who develops a partially or fully blocked airway may die if the airway is not open enough to allow enough air to reach the lungs.

The tongue is a striated muscle, which is normally maintained in a somewhat forward position under autonomic nervous control. This control, along with control of breathing and heart rate, is effected by the medulla of the brain. The autonomic control may or may not be maintained even in a person who is sleeping, semi-conscious, unconscious or under heavy sedation. Certain conditions such as severe trauma or obstruction can compromise these autonomic reflexes.

Any compromise of the oropharynx is considered to be life threatening. Such conditions can include trauma, bleeding, tumors, emesis, and a tongue and/or soft palate that can occlude the oropharynx. If a person's head is oriented with the mouth pointing upwards and the tongue is too relaxed, the tongue can move to close the person's throat, reducing or even closing the person's airway. If a severe closure condition is not corrected within several minutes, preferably within one or two minutes, this can cause a medical emergency and if the condition is not corrected within a very few minutes, it can lead to death. Blocking the airway for about two minutes can begin to reduce oxygen saturation in the brain. Maintaining the blockage for four to six minutes can begin to cause brain damage. Blocking the airway for ten more minutes can lead to irreversible brain damage.

Partial or complete unconsciousness is deliberately induced in a patient during many medical procedures. Over 24 million surgeries are performed every year in the United States alone. Many more surgeries are performed worldwide. Three general situations are of particular concern and would benefit from use of the present invention: procedures using conscious sedation or heavy sedation used in many areas of a hospital; procedures using general anesthesia; and patient management in the recovery room.

Conscious sedation involves using a short acting anesthetic medication such as nitrous oxide, propofol alfenta or fentanyl, sometimes in combination. This procedure is indicated for outpatient surgery, including oral surgery in a dentist's office, wisdom tooth extraction and such. Such a short acting medication is often administered in conjunction with an IV drip. The patient may be anesthetized for 30 minutes to about 3 hours, depending on the specific procedure. The patient generally is aroused in the office or clinic and then sent home.

General anesthesia is used daily in most hospitals. One preferred method of administrating an anesthetic is to administer a gaseous anesthetic through a mask. The mask generally covers the patient's nose and mouth. The anesthesia may be maintained for several hours, depending on the specific procedure. The oral airway currently used is frequently inadequate.

This device is more suited for general mask anesthesia because it does not irritate the airway. In the recovery room, particularly after general anesthesia, a patient is stabilized on a bed or gurney. The patient may have an obstructed airway as a result of being obtunded, with suppressed autonomic control of the tongue because of the anesthetic medication.

Another class of medical procedures would benefit from a tongue positioning device that held the patient's tongue forward. Endotracheal procedures are used frequently to visually examine the condition of many parts of a person's pharynx, larynx, trachea, lungs, esophagus and stomach. Remote manipulation devices allow surgical procedures through endoscopic devices. Placing and manipulating such devices requires getting the instruments past a patient's tongue and throat.

Yet another area of great concern is sudden infant death syndrome or SIDS. Many children born every year die in their sleep. The problem is particularly significant in premature and other low-birth-weight infants. The exact causes of death vary and are not well understood, but it appears that a significant number of deaths are caused by sleep apnea or some form of the infant's tongue blocking the airway, leading shortly to suffocation. One current treatment is to send the infant home with a sleep apnea monitoring device. A variety of such devices are available. The purpose of such a device is to detect an airway blockage or reduced or stopped breathing, to sound an alarm, and if possible to stimulate the infant and attempt to restore normal breathing. No available device works perfectly and many give frequent false alarms. Physicians in some countries, including the United Kingdom, have found the results to be so inadequate that they do not recommend using such devices. There is a need for a tongue positioning device to gently and positively maintain the infant's airway.

All of these procedures would be greatly facilitated and conditions would be alleviated if the patient's tongue could be securely and dependably maintained in a forward position, keeping the throat, and airway, open. One class of tongue positioning devices has been used for anti-snoring applications.

Prior devices for controlling snoring include those disclosed in U.S. Pat. Nos. 4,169,473 and 4,304,227 to Samelson; 4,593,686 to Lloyd et at. and 4,676,240 to Gardy. Certain of such devices provide for reception of the tongue in a hollow formed by a mouth-retained holder. One problem presented by such devices lies in the lack of fit of the device to the user's tongue; for example, mouth retention of the hollow device dictates the position of the tongue socket, whereby a longer tongue is not properly or comfortably accommodated. Such prior devices also are characterized by other problems and difficulties.

For example, U.S. Pat. No. 4,169,473 to Samelson discloses a device with a rigid tongue pocket molded to a tooth channel for positioning a user's tongue. This device offers benefits over earlier devices but does not allow breathing through the user's mouth. In addition, the simple design of the tongue chamber does not retain the tongue as well as the new invention. In another example, U.S. Pat. No. 4,676,240 to Gardy discloses a one-piece device with a deep tongue pocket, with internal ridges, external ridges to engage the user's teeth and integrally molded air tubes. The simple design of the tongue chamber does not retain the tongue as well as the new invention. In addition, unlike the new apparatus, this device is not adjustable.

One invention, disclosed in U.S. Pat. No. 5,154,184 to Alvarez, provides an improved anti-snoring device free from the problems and difficulties associated with prior devices. The apparatus includes 1) receptacle means configured for reception and retention of the outer extent of the user's tongue, and to be retained by the user's mouth, 2) shield means shaped to be received and retained outwardly of the user's lip, and 3) attachment means for adjustably attaching the shield means to the receptacle means to permit selective adjustment of the position of the shield means relative to the tongue forward extent whereby the tongue may be comfortably positioned and retained in the receptacle means, whereby snoring is reduced as the tongue is brought forward, out of the mouth, and incremental forward movement of the shield will move the tongue further forward, with lessened airway obstruction.

Typically, the receptacle means has a forward position, and the retention means projects outwardly of and about the forward position, sidewardly of the receptacle means. The shield means can extend at least partway about the receptacle means, with selective attachment to the latter. The shield may include upper and lower portions to fit outwardly of the user's upper and lower lips. The shield may be loosely carded by the receptacle means to provide breathing passages therebetween, and to allow limited tongue positioning of the receptacle means relative to the shield.

The retention means preferable includes notches presented sidewardly for selected engagement with the shield structure. In this regard, the notches may be carded by a forward portion of the receptacle structure, and are spaced to align the receptacle relative to the shield. The user begins by positioning the shield at first notches nearest the face; and the shield can be progressively advanced forwardly, away from the lips, until snoring reduction and tongue comfort are achieved.

The Alvarez '184 shield means preferably includes air holes 70 and 71 to facilitate breathing, particularly through the user's nose. However, some people prefer to breathe through their mouths. Most people suffer some restriction on nasal breathing at certain times, particularly when suffering from congestion caused by a cold or allergies. The '184 device could be improved by providing improved air communication for mouth breathing.

SUMMARY OF THE INVENTION

The present invention provides a tongue positioning apparatus with a receptacle structure configured for reception and retention of the outer extent of the user's tongue, airway structures in the receptacle structure, a shield structure shaped to be received and retained on the tongue receptacle structure and positioned just forward of the user's lip or lips, and an attachment structure for adjustably attaching the shield structure to the receptacle structure to permit selective adjustment of the position of the receptacle structure relative to the tongue forward extent whereby the tongue may be comfortably positioned and retained in the receptacle structure, whereby the tongue is brought forward. Incremental forward movement of the shield will move the tongue further forward, lessening any airway obstruction.

A preferred receptacle structure includes one or more tubes to facilitate movement of air between the user's lungs and the outside. One preferred form includes large diameter tubes, designed to admit and pass endotracheal tubes and surgical devices.

An alternate shield structure is shaped to lie along one portion of the receptacle structure to further define the airway means and further shaped to be retained just forward of the user's lip.

Another preferred receptacle structure includes a sealable, vacuum connection.

An object of this invention is to provide a tongue positioning device designed to provide easy breathing through a user's mouth.

Another object of this invention is to provide a tongue positioning device to reduce gag-reflex choking in a partially or fully unconscious person.

Another object of this invention is to provide a tongue positioning device to facilitate endoscopic procedures.

Another object of the invention is to decrease post-operative atelectasis.

Another object of the invention is to reduce incidence of SIDS.

This and other objects and advantages of the invention, as well as the details of an illustrative embodiment, will be more fully understood from the following specification and drawings.

BRIEF DESCRIPTION OF THE DRAWINGS

FIG. 8 also illustrates a detachable tether for use with this invention.

FIGS. 12A and 12B illustrate a front view of the embodiment illustrated in FIG. 11, similar to the views in FIGS. 2A and 2B, showing the shield means (12A) and receptacle (12B) when disassembled.

FIG. 13 illustrates a perspective view from the top front of another embodiment of the apparatus with two included tubes.

FIGS. 14A and 14B illustrate a front view of the embodiment illustrated in FIG. 13, similar to the views in FIGS. 2A and 2B, showing the shield means (14A) and receptacle (14B) when disassembled.

FIG. 15A also illustrates a sealable vacuum fitting.

DESCRIPTION OF THE PREFERRED EMBODIMENTS

Figure 1:
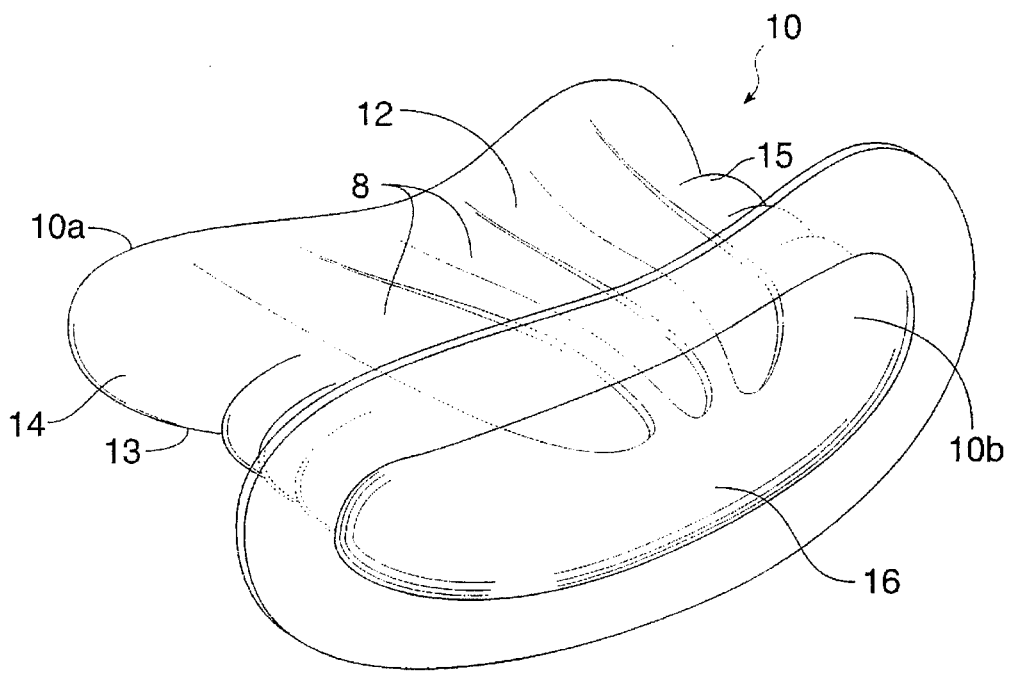
FIG. 1 illustrates a perspective view of the apparatus with a stiff shield.

In the drawings, a one-piece receptacle means is shaped for reception and retention of the forward extent of the user's tongue (not shown). To use the device, a user slips his or her tongue into the tongue receptacle. The tongue can be wiggled and pushed into the receptacle until the tongue tip reaches the maximum forward extent of the device. If air remains in the forward portion of the device, the user can wiggle his or her tongue. In addition, the forward portion of the receptacle can be gently squeezed to force air out of the forward portion. The user's tongue can relax to generally fill the forward portion of the receptacle, thereby securing the user's tongue in the device. The shield device can be fitted to the receptacle before or after inserting the tongue, although it is generally easier to attach the shield first.

Figure 2A:
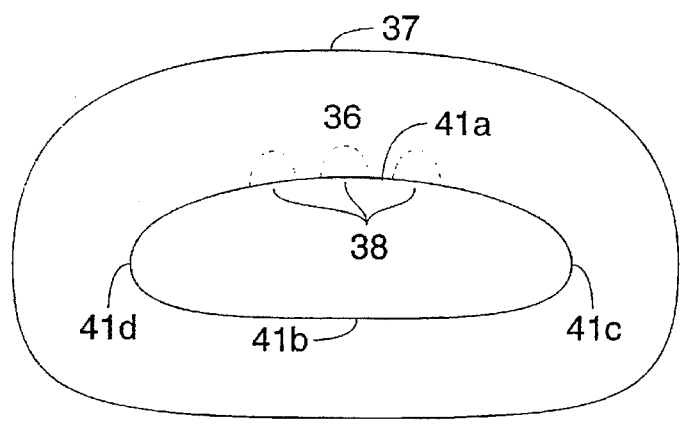
FIGS. 2A and 2B illustrate a front view taken on lines 2—2 of FIG. 3, showing the shield means (2A) and receptacle (2B) when disassembled.
Figure 2B:
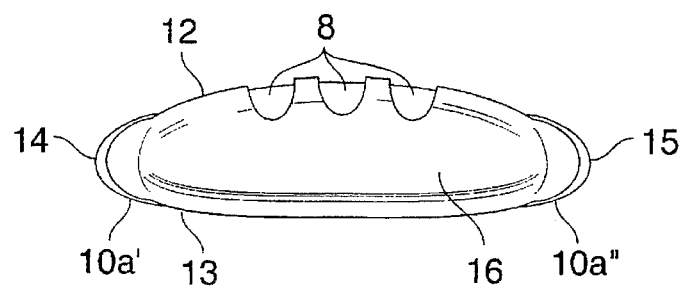
Figure 4A:
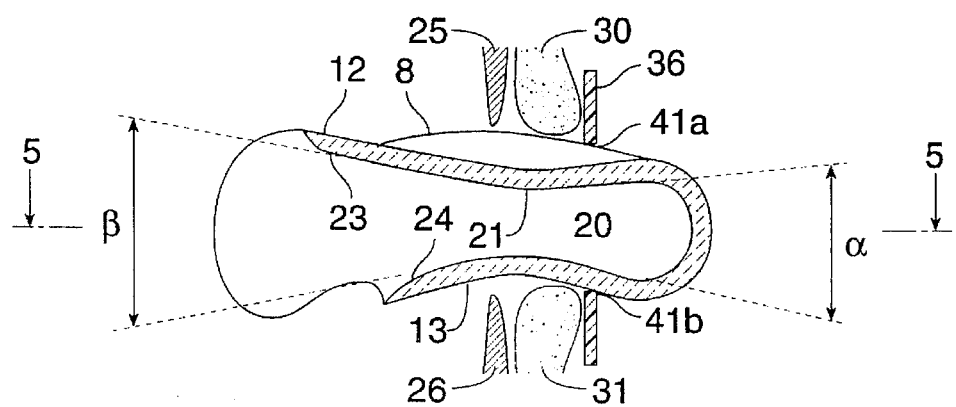
FIG. 4A illustrates a vertical section taken through the apparatus along lines 4—4 with a stiff shield when in use.
Figure 4B:
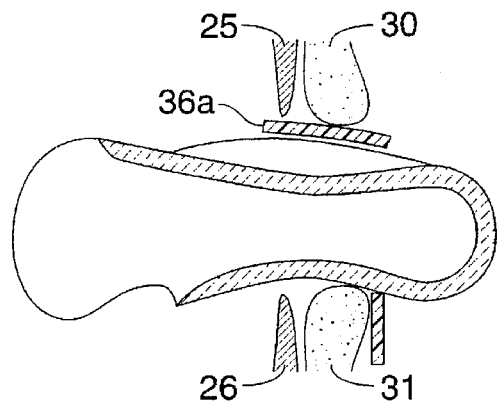
FIG. 4B illustrates a vertical section taken through the apparatus along lines 4—4 with a floppy shield when in use.
Figure 6:
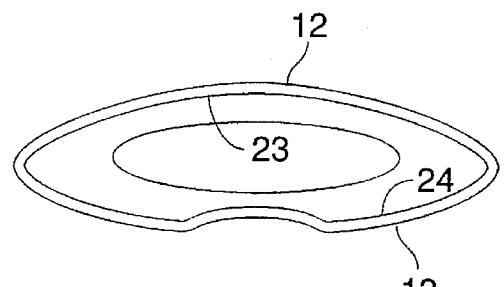
FIG. 6 illustrates a view from the rear of the receptacle.

Referring to FIGS. 1 and 2B, such receptacle means 10 has a rearward section 10a which is "C" or crescent-shaped along the bottom wall 13 and generally flat along top wall 12. The receptacle has a pocket-shaped forward section 10b integral with 10a. The forward section has upper and lower generally parallel walls 12 and 13, opposite side walls 14 and 15, which are outwardly convex, and a front wall 16, which is forwardly convex and merging with 12 and 13, and with 14 and 15. Referring to FIGS. 4A, 4B and 6, forward section 10b is sized to project forwardly of the user's lips with the tongue resting comfortably, substantially filling the cavity or compartment 20 defined by walls 12–16.

Upper and lower walls 12 and 13 flare forwardly at a small angle α (see FIGS. 4A, 4B, 6) from a narrowed region 21 at the proximate joinder of sections 10a and 10b. Similarly, right and left walls 14 and 15 flare forwardly at a small angle α from a narrowed region 22 at the proximate joinder of sections 10a and 10b. Region 21 and region 22 may be at approximately the same anterior position between the front and back of the apparatus, forming an annular constriction, but can be at different anterior positions. These regions together define a sort of hourglass shape, which provides a mild constriction around the tongue. The tongue forward of this restriction tends to expand slightly and fill substantially all of compartment 20. This provides mechanical retention of the tongue in addition to the simple vacuum effect relied on by prior art devices with generally straight interior chambers. In addition, since the apparatus is often made of elastomeric material, if the user clenches down on the apparatus, however lightly, this will tend to deform the apparatus and further narrow the constriction, providing additional mechanical retention. The restriction preferably is positioned so the anterior third of the tongue can expand anterior to the restriction.

Angle α may range from generally widening, up to about 50°, to flat or even somewhat negative (narrowing) such as about −10°, and preferably is between about 2° and 10°. Angle α', like angle α, may range from generally widening, up to about 50°, to flat or even somewhat negative (narrowing) such as about −10°, and preferably is between about 2° and 10°. Angle α' and angle α are independent and so may be similar or different.

The rearward section 10a has interior upper wall 23 and interior lower crescent wall 24 that flare apart rearwardly at an angle β and interior left wall 27 and interior right wall 28 flare apart, rearwardly, at an angle β' to accommodate the user's tongue and fit the user's mouth. Angle β preferably is greater than angle α and angle β' preferably is greater than angle α' and each of these angles are independent. Each of angles β and β' may vary between about 0° and 60° but preferably is between about 15° and 35°.

Figure 5:
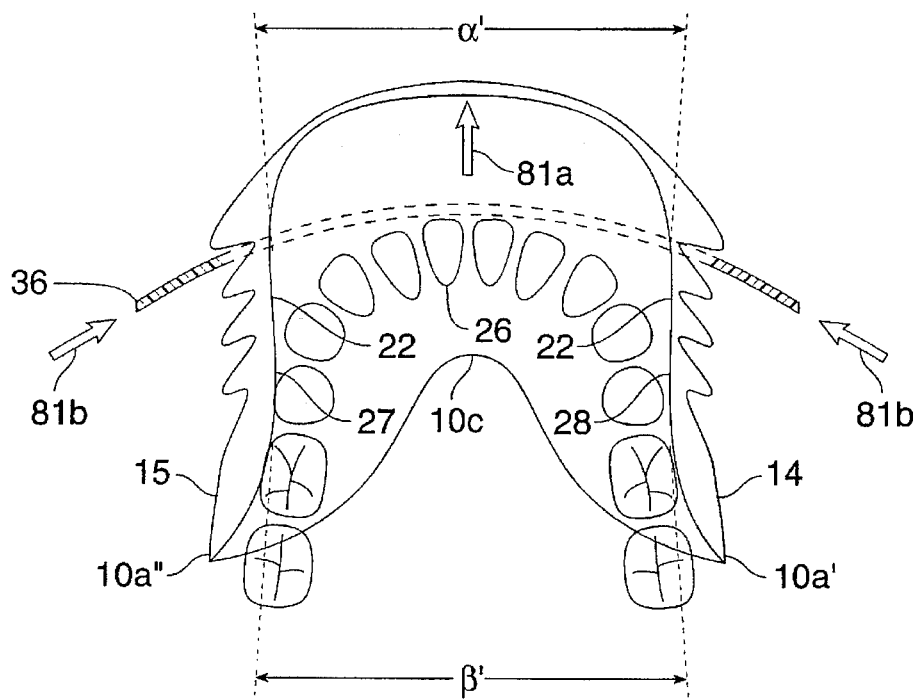
FIG. 5 illustrates a sagittal section taken through the apparatus.

The lower portion of rearward section 10a has laterally extending and rearwardly diverging subsections or lobes 10a' and 10a" which are adapted to fit the rearward curvature of a user's left and right lower teeth regions. Concave extent 10c provides relief for the lingual frenulum and the floor of the mouth of the user. This relief is particular important for users with certain mouth geometries. Referring to FIG. 5, some portion of the user's teeth rest on the top and bottom of the apparatus, keeping it away from the floor or roof of the user's mouth.

One or more channels 8 are provided in upper portion 12. Each channel preferably begins in a region near the front of the apparatus which will be in front of the user's lips and extends backwards to a region which will be behind the user's teeth. Each channel 8 provides an air passage to facilitate breathing through the user's mouth. In a preferred embodiment, three channels 8 are provided, positioned so a typical user's teeth will engage the apparatus to rest on upper surface 12 and to not occlude any channel 8. Alternatively, one or more channels may be designed into the bottom or one or both sides of the new apparatus.

Even without channels 8 a user's mouth often will allow some air to enter, for example at the side where the lips come together with the apparatus. However, it is important in many situations to have dependable air channels for easy mouth breathing. In various medical conditions, an airway can be guaranteed by inserting an endotracheal tube. This is sometimes described as airway patency. A single tube with 7 $mm^2$ internal cross section is accepted as a minimum for a normal adult. In the present apparatus, the cumulative cross section of channels 8 preferably is in excess of this value. In one preferred embodiment, each of three channels has a minimum cross section of 4.2 $mm^2$ and a maximum cross section of 4.5 $mm^2$ for a total of 12.6–13.5 $mm^2$. The channel cross section for children and infants can be adjusted according to teachings in the art.

Figure 9A:
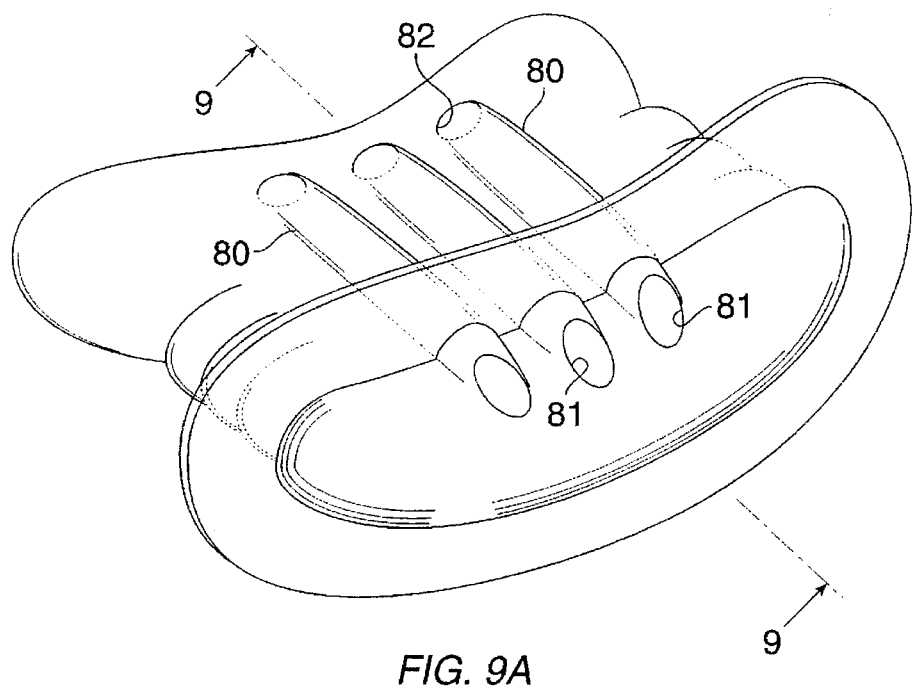
FIG. 9A illustrates a perspective view from the top front of an embodiment of the apparatus with three included tubes.
Figure 9B:
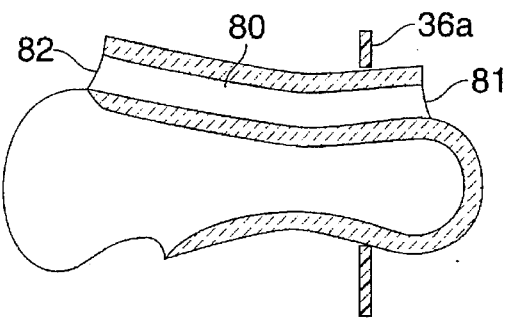
FIG. 9B illustrates a vertical section taken through the apparatus along lines 9—9.
Figure 11:
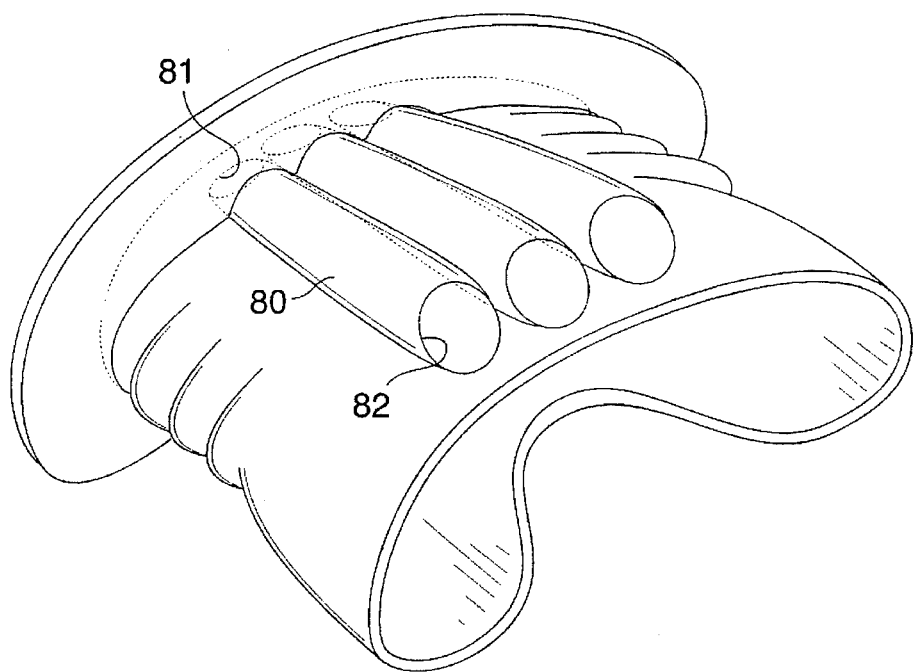
FIG. 11 illustrates a perspective view from the top rear of another embodiment of the apparatus with three included tubes.
Figure 12A:
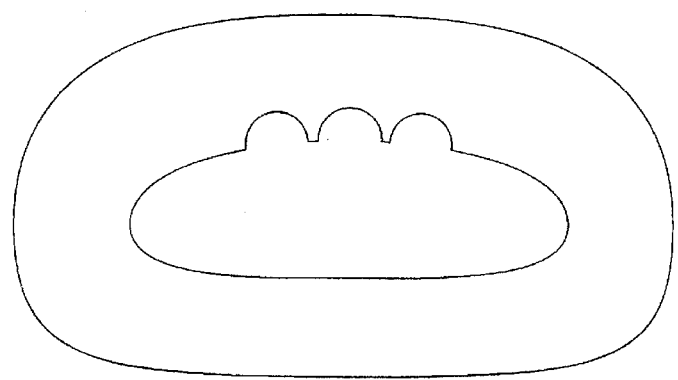

Referring to FIGS. 9A and 9B, one preferred embodiment includes one or more tubes 80 which may be attached to or integrated into receptacle 10. Each of tubes 80 has an opening 81 outside the user's mouth and an opening 82 inside the user's mouth. FIG. 11 illustrates an alternate embodiment with three, larger diameter tubes 80. FIG. 13 illustrates an alternate embodiment with two, still larger diameter tubes 80.

In use, the user will tend to push the device upwards towards the top of his or her mouth. Opening 82 preferably is not bevelled at an angle which might align with the roof of the user's mouth. If such a bevel were present, opening 82 could align with the soft or hard palate and close off tube 80. One useful angle for opening is approximately perpendicular to upper surface 12 of receptacle 10.

The apparatus may be constructed of a variety of materials well known in the medical and dental fields. A preferred composition is molded silicone, preferably of medical grade. Other useful materials include latex, polystyrene, vinyl acetate, polyethylene and polypropylene. Elastomeric materials are preferred. A material with a durometer between about 5 to 50 is generally useful, most preferably with a durometer of about 20–30. It is possible to use a hard, non-pliable material to make the present device, but the materials already described are preferred.

The thickness of the material can be varied depending on the specific material used, but the thickness should be sufficient to allows the apparatus to be fairly rigid, but somewhat pliable. The material should not be so thin so as to make the apparatus difficult to manufacture or so thick that the apparatus forces the user's mouth open unnecessarily. For silicone, a thickness of about 0.5 to 7 millimeters, preferably 0.5 to 4 mm and more particularly about 2 to 3 mm is particularly useful.

In one preferred embodiment, the user places his or her tongue in the receptacle and positions the receptacle so narrowed region 21 is close to the user's incisors. The user's other teeth then rest on portion 10a of the apparatus. Since the apparatus is tapered towards narrowed regions 21 and 22, any teeth resting on the rearward portions of the apparatus will tend to push the apparatus forward. This then moves the tongue forward and achieves the desired effect.

The device is particularly beneficial because the user is not placed in an unnatural or uncomfortable position. In general, the apparatus moves the tongue forward about 1 to 4 centimeters, which is sufficient to maintain a patent airway in most people. This allows a useful air opening for use with medical procedures requiring a patent airway, such as general anesthesia. This is well within the normal range of tongue extension, roughly comparable to ticking ones tips. The user will sleep with his or her mouth open slightly, but this is also within the normal range of motion for typical user. With the apparatus naturally positioned, the user will press tightly on their own tongue, through 5–6 mm of elastomeric material. This amount of mouth opening is less than is encountered in normal speaking of an open vowel such as "ah." Thus the apparatus can be worn without discomfort.

Figure 2C:
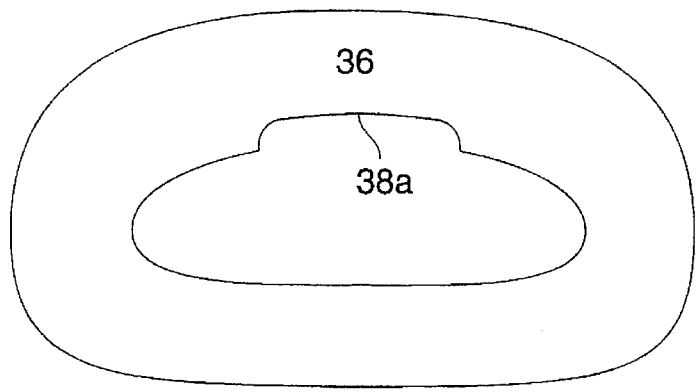
FIG. 2C illustrates an alternate form of the shield.

In accordance with a further aspect of the invention, a shield or retention means is provided, shaped to be retained outwardly of the user's lower lip. As illustrated in FIG. 2A, the shield means preferably has the form of a shield 36 of outer edge outline 37 with inner edge outline 41 designed to accommodate receptacle means 10. The receptacle means and shield are separate parts to be relatively adjustable for mouth and tongue comfort, and preferably are similar in thickness. The shield means preferably is made of a sterilizible, hard material, such as plastic. One preferred material is polycarbonate. One preferred method of sterilization is cold sterilization, widely available in dental and medical offices. The shield can also be cleaned with isopropyl alcohol. FIG. 2C illustrates an alternative form of shield 36.

Figure 15A:
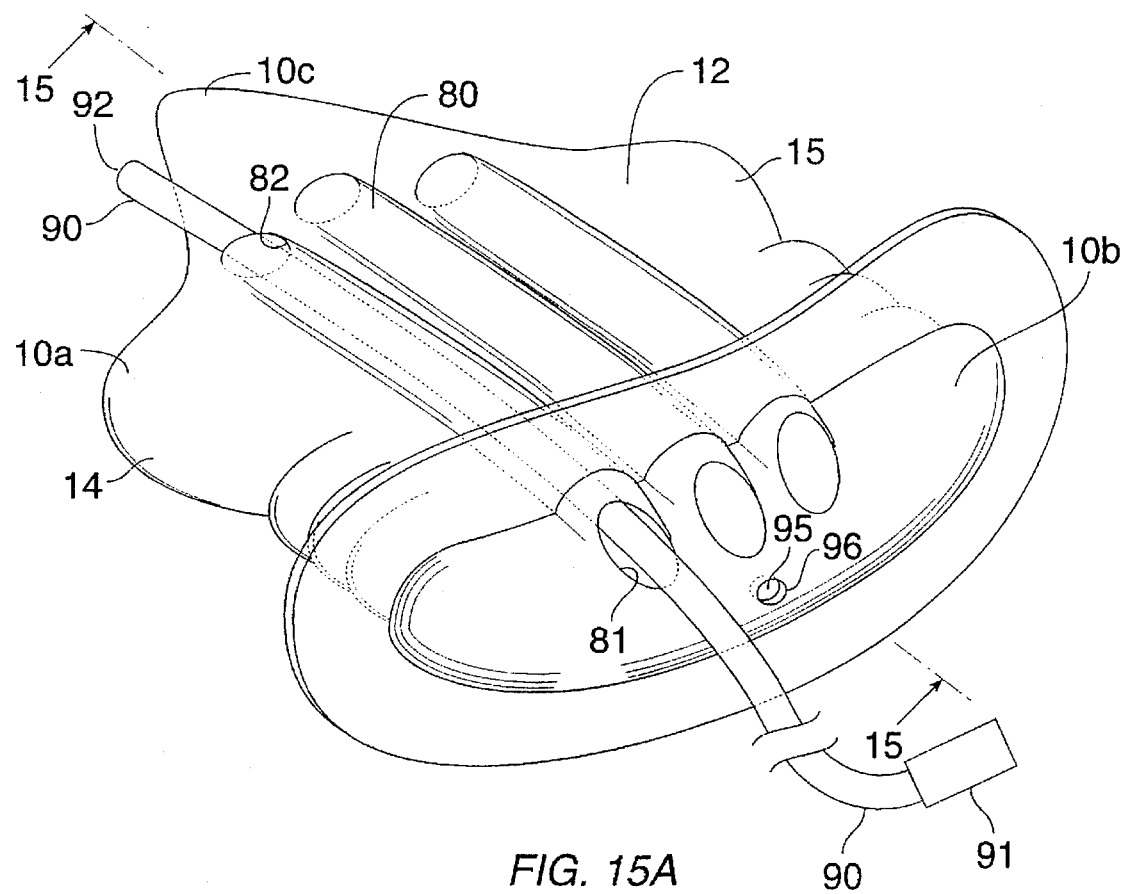
FIG. 15A illustrates a perspective view from the top front of another embodiment of the apparatus with three included tubes and a rear extension, with an endoscopic device positioned through one of the holes.
Figure 15B:
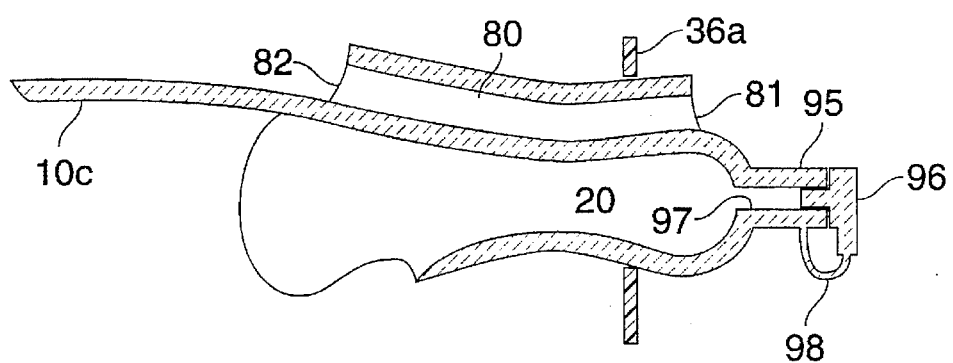
FIG. 15B illustrates a vertical section taken through the apparatus of FIG. 15A along lines 15—15.

The shield defines a generally oval shaped opening to receive and fit over the forward section 10b of the receptacle means, in an adjustable manner, and may engage the user's upper and lower tips. Note inner edge 41 of that opening, having elongated upper and lower portions 41a and 41b concave and adapted to fit along 12 and 13 respectively (see FIGS. 3, 4A and 4B). Left portion 41c and right portion 41d are curved and adapted to fit notches described below. In one alternate embodiment, portions 41c and 41d include a generally straight portion. FIGS. 9B and 15B illustrate alternate embodiments of shield 36 positioned on various preferred forms of receptacle 10.

Figure 10A:
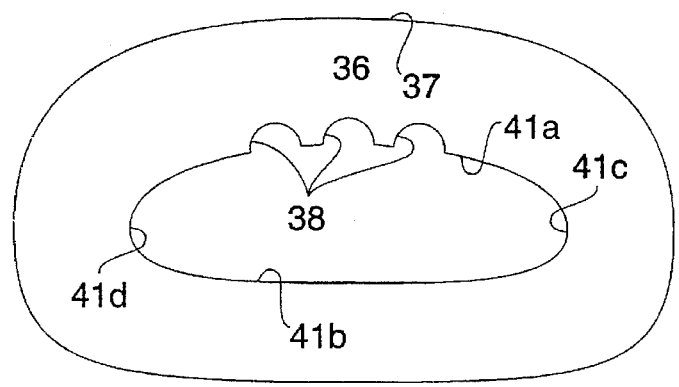
FIGS. 10A and 10B illustrate a front view of the embodiment illustrated in FIG. 9A, similar to the views in FIGS. 2A and 2B, showing the shield means (10A) and receptacle (10B) when disassembled.
Figure 10B:
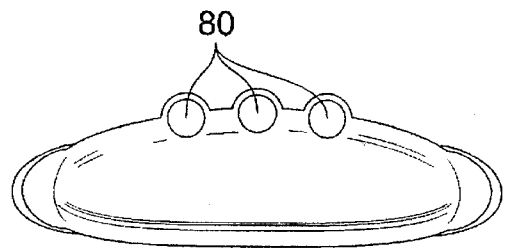

Air channels 8 allow mouth breathing while the apparatus is being worn. In one embodiment of the apparatus, notches 38 are provided to generally align with channels 8 to provide even greater air flow. Notches 38 should not be so deep as to compromise the mechanical integrity of the shield 38. Notches 38 preferably are not deeper than the smaller of 5 millimeters and half the width of shield means 36. Still more preferably notches 38 are not deeper than the smaller of 3 millimeters or one third the width of shield means 36. FIGS. 10A and 10B illustrate a preferred embodiment of shield 36 for receptacle 10 including tubes 80. FIGS. 12A, 12B, 14A and 14B illustrate alternative forms of shield 36 and receptacle 10.

Figure 3:
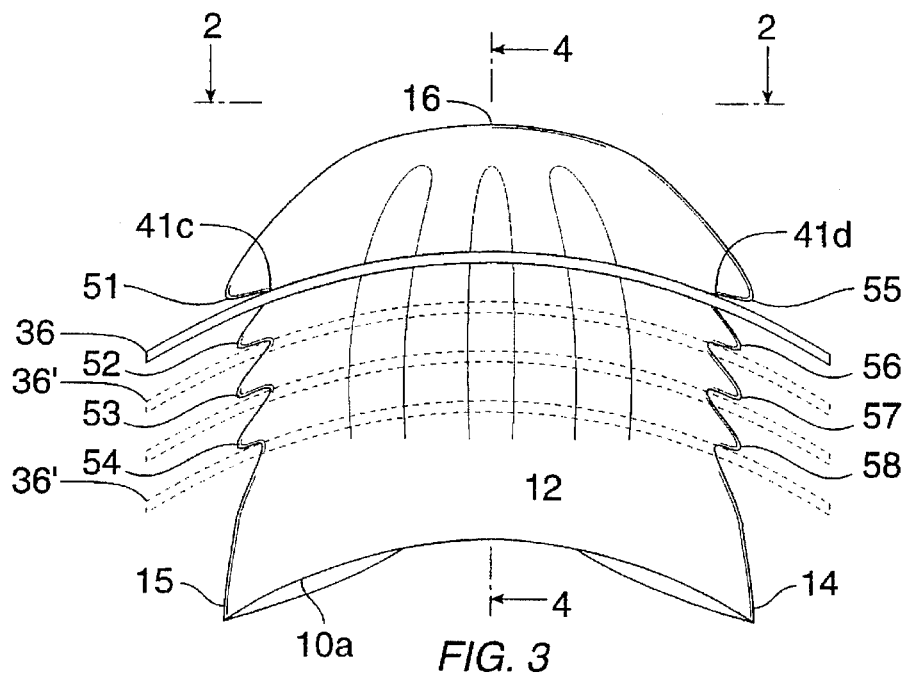
FIG. 3 is a top plan view of the apparatus incorporating the invention.

Attachment means is provided for adjustably attaching the shield means to the receptacle means, to permit selective adjustment of the position of the receptacle means relative to the tongue forward extent whereby the tongue may be comfortably positioned and retained in the receptacle means. Such attachment means may advantageously take the form of notches presented sidewardly of the receptacle means. Referring to FIG. 3, forwardly and rearwardly spaced ridges 51, 52, 53 and 54 which define a series of notches at side 14 of 10b, and forwardly and rearwardly spaced ridges 55, 56, 57 and 58 which define a series of notches at side 15 of 10b. Ridges 51 and 55 preferably are some amount taller or longer than the others in order to provide a greater resistance to removing the shield from the last notch, which would remove it entirely from the apparatus.

The shield edge 41c is seen adjusted rearwardly to fit the notches between 51 and 52 in FIG. 3, and edge 41d fitting the notch between 55 and 56. If desired, the flexible shield can be adjusted rearwardly (see broken lines 36') so that its edge 41c fits the notch between 52 and 53, and edge 41d between 56 and 57 as well as additional positions further rearward. Thus, comfortable retention of the wearer's tongue, as during sleep, is facilitated while breathing through a channel 8 remains possible. In this regard, the shield is retained in position on the receptacle which is retained in position by the mouth, and the tongue is positioned comfortably in and by the receptacle, which may be adjusted relative to the shield, as desired. The user's lips are free to flex and are not outwardly constrained or overlain by the apparatus.

The shield means is preferably curved to conform to the shape of a human face. The notches preferably are shaped to curved to accept the curve of the shield means. This curve improves the effectiveness of the notches as well. Referring to FIG. 5, if the user pulls back on the apparatus, for example by trying to remove the tongue, the lips press shield 36 forward with force 81a. This in turn applies forces 81b to urge interior shield portions 41c and 41d into close proximity to the notches.

Figure 7:
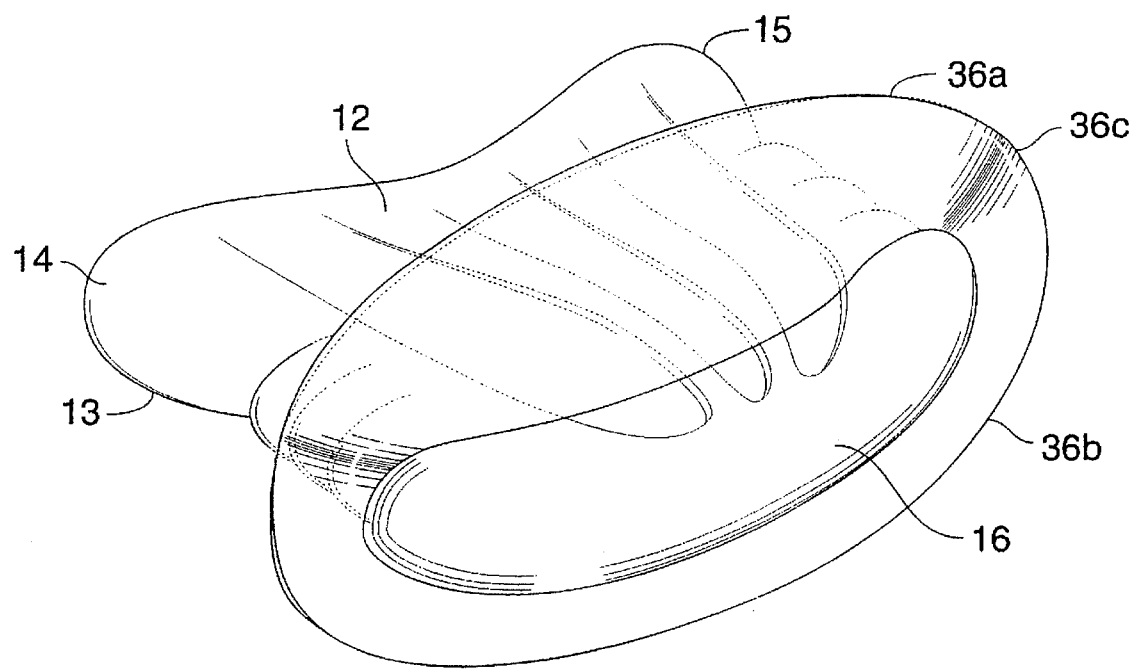
FIG. 7 illustrates a perspective view of the apparatus with a floppy shield.
Figure 8:
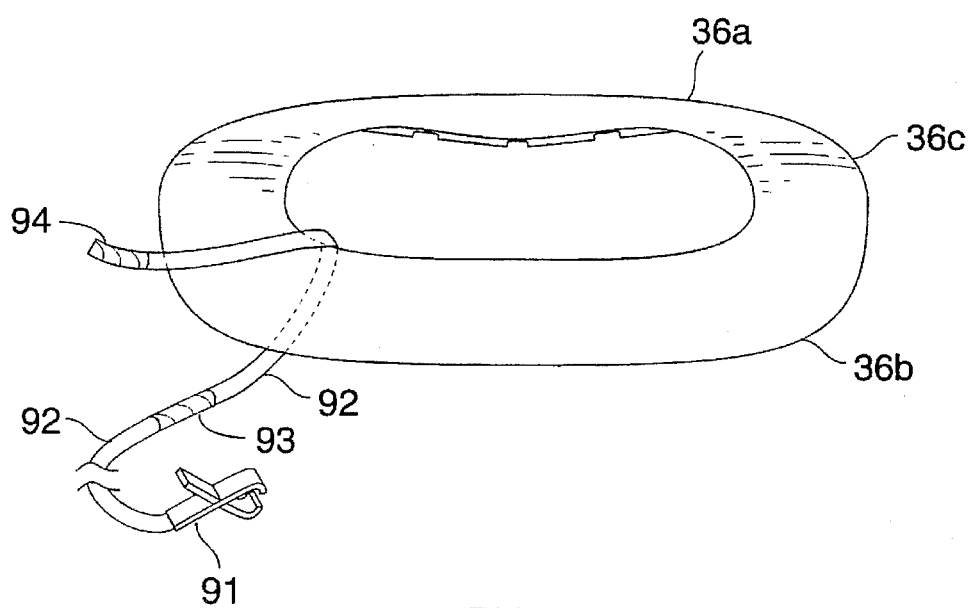
FIG. 8 illustrates a front view similar to FIG. 2A showing a floppy shield means when disassembled.

In an alternate preferred embodiment, illustrated in FIGS. 7 and 8, the shield is designed to provide a floppy shield which incorporates some generally soft material so the uppermost portion 36a and lowermost portion 36b of shield 36 can fold at a hinge region 36c. This allows uppermost portion 36a to lie generally parallel to top portion 12 of the receptacle. This closes each channel 8 to define a complete channel with easy communication between the inside of a user's mouth and the outside. The user's lower lip will be behind lowermost shield portion 36b and the user's upper lip should be in a generally parallel position along the top of the apparatus. Upper portion 41a of the inside edge of shield 6 should extend past the user's top lip to keep at least one channel 8 open to the outside air.

Once the user's tongue is in the receptacle and the shield means is in place, the user's lower lip presses lightly against the shield means, compressing the lip slightly. When using the upright shield 36, the user's upper lip will be slightly compressed as well.

Use of the new device facilitates nasotracheal intubation of a user/patient. With the patient's tongue positioned, a physician can readily introduce a nasotracheal, nasogastral, or other tube. Without tongue positioning, the tube must be lubricated and the patient must swallow repeatedly as the tube is introduced to urge the tube down the patient's throat. With tongue positioning, lubrication may still be helpful, but little if any swallowing is required to introduce the tube. This makes the patient much more comfortable and makes the procedure faster and safer.

Tongue positioning facilitates use of gaseous anesthesia. With the throat maintained in an open position, gas introduced through a face mask is readily communicated to the user/patient's lungs, and thence into the bloodstream. In addition, the airway is stabilized so the anesthesiologist does not have to worry as much about the patient gagging or choking while under the effect of the anesthetic. If the anesthesiologist chooses to intubate for an assured airway, the intubation procedure is easier because the throat is open. For use with an anesthesia mask, the shield should not be so wide as to interfere with the normal positioning and operation of the mask. A variety of shield shapes and sizes can be provided to accommodate a variety of patients and physical characteristics, but in general one or two generic sizes will be useful with most adults. The device can be manufactured in pediatric and infant sizes as well.

Tongue positioning largely obviates the need to intubate patients in a recovery room. In some conditions, it may be preferable to intubate the patient even with the tongue positioning device in place, but for most patients and conditions, the device alone will guarantee a patent airway so a recovering patient will not lose airway accidentally.

In accordance with a further aspect of the invention, an extension can be added to protect a user's tongue during an endoscopic procedure. Referring to FIGS. 15A and 15B, rear portion 10a of receptacle 10 can be extended with extension 10c to cover more of the user's tongue. A variety of exact shapes can be used and will be understood by one skilled in the art. Working end 92 of endoscope 90 can be passed through front opening 81 of a tube 80, through tube 80 and out through rear opening 82 along extension 10c. The physician can use manipulation controls 91 to guide endoscope 90 across extension 10c with minimal discomfort to the patient. Since shield 36 can be positioned to pull the tongue forward, this makes the throat opening larger and the physician can guide endoscope 90 along extension 10c, then further along the patient's tongue and down the throat. Extension 10c may extend far enough to cover part of the tongue past the epiglottis to provide some tongue protection during intubation with a nasotracheal tube.

Figure 16:
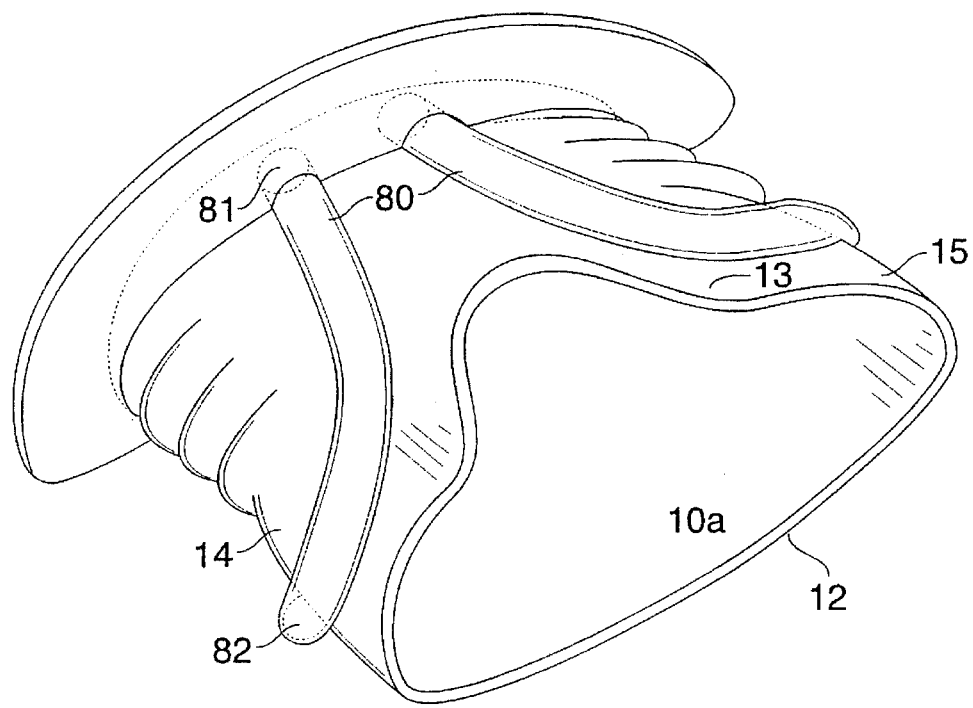
FIG. 16 illustrates a perspective view from the rear bottom of another embodiment of the apparatus with two included tubes on the bottom of the receptacle.
Figure 17A:
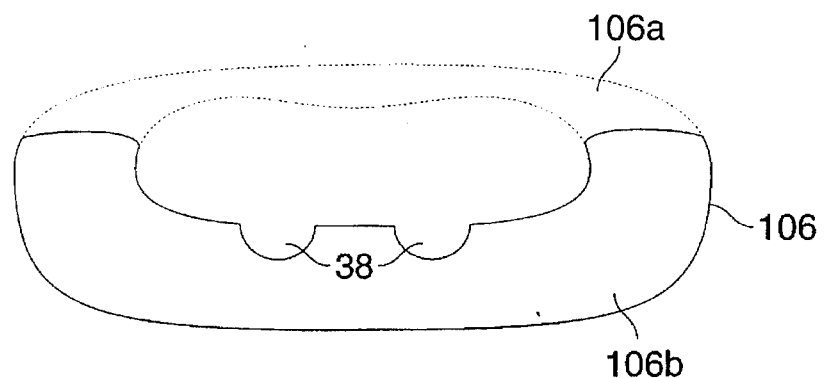
FIGS. 17A and 17B illustrate a front view of the embodiment illustrated in FIG. 16, similar to the views in FIGS. 2A and 2B, showing the shield means (17A) and receptacle (17B) when disassembled.
Figure 17B:
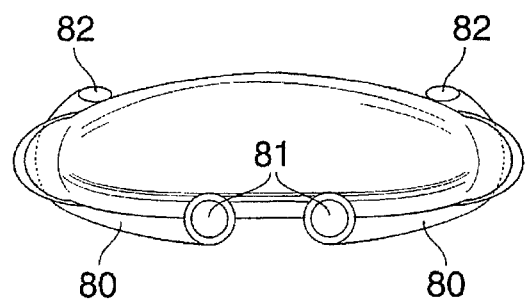

Referring to FIGS. 16, 17A and 17B, another preferred form of the apparatus includes one or more tubes 80 on the bottom of receptacle 10 which curve around receptacle to connect outside air at inlet 81 to outlet 82 inside the user's mouth. This is particularly useful in conjunction with shield 106 which has lower portion 106b but little (dotted line) or no upper portion 106a. This apparatus is useful in practicing some oral surgeries.

In accordance with yet a further aspect of the invention, a vacuum fitting can be provided to facilitate drawing air from within the forward section of the tongue receptacle. Referring to FIGS. 15A and 15B, forward section 10b of receptacle 10 can be fitted with vacuum fitting 95 connecting with compartment 20 in forward section 10b. Vacuum fitting 95 can be reversibly sealed by a variety of apparatuses and methods known in the art. FIG. 15B illustrates plug 96 secured by integral tether 98 and fitted inside vacuum channel 97 to seal vacuum fitting 95. Alternative valve devices include slidable valves and one way valves.

The basic device, without the vacuum fitting, can be secured readily by a conscious user. In typical use, the user will position the shield on the receptacle, then insert his or her tongue into the receptacle. The forward portion of the receptacle can be gently squeezed, as needed, to expel entrapped air.

However, if the user is unconscious, uncommunicative, or uncooperative it may be more difficult to position the device. This is particularly true for anesthetized individuals or infants. Adding the vacuum fitting allows the user or a second person to connect the fitting to a source of vacuum, roughly position the user's tongue, apply a vacuum to pull the tongue into the receptacle, and then close off the vacuum fitting. The valve means should be easily sealable so as to maintain the user's tongue in position in the receptacle. Suitable sources of vacuum include a variety of suction devices found in many medical environments, as well as a detachable tube to which a person can apply vacuum by sucking. In some applications, a second person may simply position his or her mouth directly on the vacuum fitting and apply negative pressure.

The vacuum fitting is particularly useful in certain applications. In a surgical setting, if an anesthesiologist notices that the patient's tongue is slipping out of the receptacle, the anesthesiologist can apply vacuum to reposition the tongue. For an infant, particularly one at risk of sudden infant death syndrome, a parent or other person can place the receptacle over an infant's tongue, then gently apply negative pressure to position the infant's tongue in the receptacle.

The addition of the vacuum fitting makes the device useful for veterinary applications. The receptacle can be manufactured in a shape suitable for a specific animal species, then secured by a variety of means including the shield but also including other positioning devices recognized by those skilled in the art.

Referring to FIG. 8, in yet another embodiment of the invention, a first securing means such as clip 91 is connected through tether means 92 to a second securing means such as a looped strap with hook and loop portions 93 and 94. The first securing means can be secured to an article of clothing worn by the user. The second securing means can be secured to the apparatus, for example by passing part of the tether around shield means 36a and connecting hook and loop portions 93 and 94 to for a loop of tether. This allows ready recovery of the apparatus in case it is accidentally removed from the user's mouth. This is particularly helpful in case the apparatus slips out at night while the user is sleepy and may not be aware of where the apparatus may have ended up. This is also helpful in many care-giving situations for the aged, paraplegic, handicapped or others with compromised manual dexterity. This or a similar tether can be used in combination with other receptacle and shield combinations described above.

The apparatus has the following advantages:

1. The generic design of the apparatus can fit most user's without modification, thus reducing the cost to the user. The apparatus is so designed that is does not need the services of a professional for adaptation to an individual. It can be self-fitted by the user for maximum benefit.

2. The tongue compartment may be made in multiple sizes, e.g., medium, large and extra large, to better accommodate a variety of tongue sizes. Smaller sizes for pediatric and infant applications can also be provided.

3. The tongue pouch is so designed as to allow better tongue control, by grasping and keeping it in a protrusive position determined by a labial shield.

4. The method for extending the tongue is controlled by notches along each side of the tongue compartment.

5. The overall size of the appliance is relatively small, thus more comfortable. It relieves psychological stress, allowing muscles to relax and to open the patient's airway.

6. The design of the tongue retention shield allows those who are mouth breathers to breathe normally, without need for bulky airways. It is also easy to breathe around the apparatus.

7. The appliance is designed in the posterior area to allow minimal vertical opening, which will avoid TMJ problems.

8. The thickness, in the posterior region, of the apparatus material is such that it will prevent damage caused by bruxism.

9. The appliance may be made in colors so that it may be identified easily. It may be designed to be opaque or generally translucent, which makes it more attractive to wear.

10. The apparatus is marked so that it cannot be inserted in the wrong manner, and with holes for breathing and reinforcement flanges to determine the correct position.

A general description of the apparatus and method of using the present invention as well as a preferred embodiment of the present invention has been set forth above. One skilled in the art will recognize and be able to practice many changes in many aspects of the apparatus and method described above, including variations which fall within the teachings of this invention. The spirit and scope of the invention should be limited only as set forth in the claims which follow.

What is claimed is:

1. In a tongue positioning apparatus, the combination comprising a) a tongue receptacle means having a top surface configured for reception and retention of forward extent of the user's tongue, and to be retained by the user's mouth, b) a tube configured to receive an elongated device useful in a medical procedure secured to said receptacle, said tube communicating with the interior of the user's mouth and outside the patient's mouth when the apparatus is positioned for use, c) a removable shield means shaped to be received and retained outwardly of the user's lip having a shelf unitary with the shield means and extending at an angle from the shield which is configured to receive the user's lips, d) attachment means for attaching the shield means to said receptacle means to permit positioning the shield means and the shelf relative to the tongue forward extent whereby the tongue may be comfortably positioned and retained in said receptacle means, whereby the tongue is brought forward, out of the mouth, and forward movement of the shield will move the tongue so as to allow improved access to the patient's oropharynx with an elongated tube inserted through the tube, and (e) an extension on the top surface of the tongue receptacle means having a length sufficient to cover the user's epiglottis when the apparatus is positioned on the user's tongue.

2. The tongue positioning apparatus of claim 1 wherein said attachment means includes attachment means for adjustably attaching the shield means to said receptacle means to permit selective adjustment of the position of the shield means relative to the tongue forward extent.

3. The tongue positioning apparatus of claim 1 wherein the shield means does not completely encircle the receptacle means.

4. The tongue positioning apparatus of claim 3 wherein said walls flare rearwardly of said notches.

5. The tongue positioning apparatus of claim 1 further comprising vacuum applying and maintaining means connected to said receptacle.

6. The tongue positioning apparatus of claim 1 further comprising a plurality of said tubes.

7. The tongue positioning apparatus of claim 1, wherein the tube has a diameter sufficient to accommodate an endoscopic device.

8. A method of using a tongue positioning apparatus in a medical procedure on a patient comprising the steps of:

providing a tongue positioning apparatus as claimed in claim 1, placing the tongue positioning apparatus on the tongue of the patient to move the tongue forward and provide access to the patient's oropharynx through the tube, introducing an elongated device through the tube, and performing a medical procedure with the elongated device.

9. The method of claim 8, wherein the step of introducing an elongated device comprises introducing a device for performing an endoscopic procedure.

10. The method of claim 8, wherein the step of performing a medical procedure comprises administering a gaseous anesthetic.

11. The method of claim 8, wherein the step of performing a medical procedure comprises intubating the person.

* * * * *